US011505584B2

(12) United States Patent
Schneiderman et al.

(10) Patent No.: US 11,505,584 B2
(45) Date of Patent: Nov. 22, 2022

(54) THERAPY FOR REDUCING BRAIN DAMAGE

(71) Applicants: REMODELESS CV LTD, Kiriat Ono (IL); TRUSTEES OF BOSTON UNIVERSITY, Boston, MA (US)

(72) Inventors: Jacob Schneiderman, Kiryat Ono (IL); Florian Douam, Brighton, MA (US)

(73) Assignees: REMODELESS CV LTD, Kiriat Ono (IL); TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 17/235,968

(22) Filed: Apr. 21, 2021

(65) Prior Publication Data

US 2021/0324021 A1 Oct. 21, 2021

Related U.S. Application Data

(60) Provisional application No. 63/012,927, filed on Apr. 21, 2020, provisional application No. 63/061,210, filed on Aug. 5, 2020.

(51) Int. Cl.
| | |
|---|---|
| *C07K 14/47* | (2006.01) |
| *A61K 9/00* | (2006.01) |
| *A61P 31/14* | (2006.01) |
| *A61K 38/00* | (2006.01) |

(52) U.S. Cl.
CPC ........ *C07K 14/4702* (2013.01); *A61K 9/0075* (2013.01); *A61P 31/14* (2018.01); *A61K 38/00* (2013.01)

(58) Field of Classification Search
CPC ................ C07K 14/4702; C07K 16/22; C07K 16/2863; C07K 16/32; C07K 2317/55;
(Continued)

(56) References Cited

U.S. PATENT DOCUMENTS

2012/0142585 A1* 6/2012 Otvos ................ A61K 39/0005
514/19.5
2012/0263680 A1* 10/2012 Lander .................. A61K 38/10
424/85.5
(Continued)

FOREIGN PATENT DOCUMENTS

WO 2011132189 12/2011

OTHER PUBLICATIONS

Van der Voort, P.H.J et al in Heliyon, Aug. 6 (8), e04696, 2020.*
(Continued)

*Primary Examiner* — Gollamudi S Kishore
(74) *Attorney, Agent, or Firm* — Soroker Agmon Nordman

(57) ABSTRACT

Embodiments of the disclosure provide a method for treatment of damaged lung tissue, e.g., lungs of a patient with a viral infection (e.g., coronavirus) and/or a bacterial infection and/or a parasitic pathogen or a patient whose lung tissue was damaged by exposure to a chemical, and a patient with acute respiratory distress syndrome (ARDS). Also provided is a method for protecting the brain from neuro-invasion and preventing inflammatory damage to organs remote from the lungs, by blocking cytokine synthesis in the lungs. The treatment includes administering a leptin antagonist (LepA) locally to the upper airways and/or to the lungs of the patient. Typically, the LepA is administered in an inhalable composition, such as, an aerosol.

10 Claims, 8 Drawing Sheets

LepA treatment reduces lung and brain viral load

(58) Field of Classification Search
CPC .... A61K 9/0075; A61K 38/00; A61K 38/191; A61K 9/0019; A61K 38/179; A61K 38/1866; A61K 38/40; A61K 47/6911; A61K 47/6913; A61K 9/1271; A61K 9/1272; A61P 31/14
See application file for complete search history.

(56) References Cited

U.S. PATENT DOCUMENTS

| | | | |
|---|---|---|---|
| 2014/0037697 A1* | 2/2014 | Kordikowski | A61P 37/08 424/400 |
| 2014/0296141 A1* | 10/2014 | Lee-Huang | A61K 31/4439 514/6.5 |
| 2015/0329635 A1* | 11/2015 | Suratt | G01N 33/74 424/158.1 |

OTHER PUBLICATIONS

"Development and characterization of high affinity leptins and leptin antagonists." J. Biol Chem. Feb. 11, 2011:286 (6):4429-42. Shpilman M, Niv-Spector L, Katz M, Varol C, Solomon G, Ayalon-Soffer M, Boder E, Halpern Z, Elinav E, Gertler A.

The role of leptin in the respiratory system: an overview. Respir Res. Oct. 31, 2010;11(1):152. doi: 10.1186/1465-9921-11-152. PMID: 21040518; PMCID: PMC2988727. Malli, F., Papaioannou, A.I.; Gourgoulianis, K.I. et al.

Leptin as regulator of pulmonary immune responses: involvement in respiratory diseases. Pulm Pharmacol Ther. Aug. 2013;26(4):464-72,Epub Mar. 27, 2013. Vernooy JH, Ubags ND, Brusselle GG, Tavernier J, Suratt BT, Joos GF, Wouters EF, Bracke KR.

Benbenishty, A., & Schneiderman, J. (2022). Intraarterial anti-leptin therapy via ICA protects ipsilateral CA1 neurons subjected to ischemia and reperfusion. Plos one, 17(1), e0261644.

* cited by examiner

LepA treatment reduces lung and brain viral load

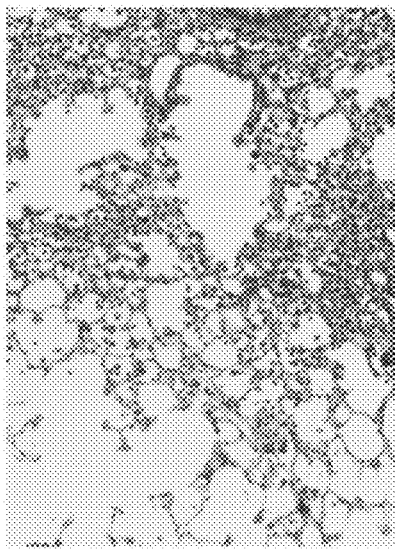
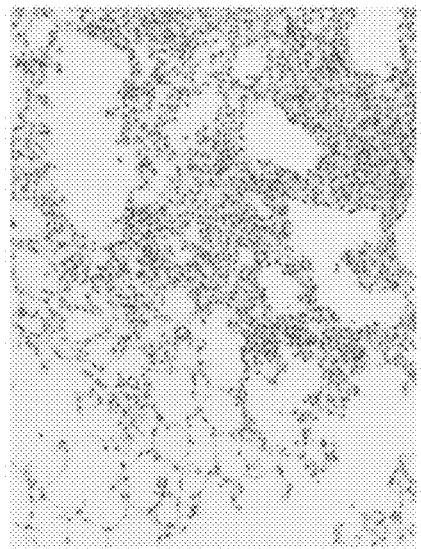
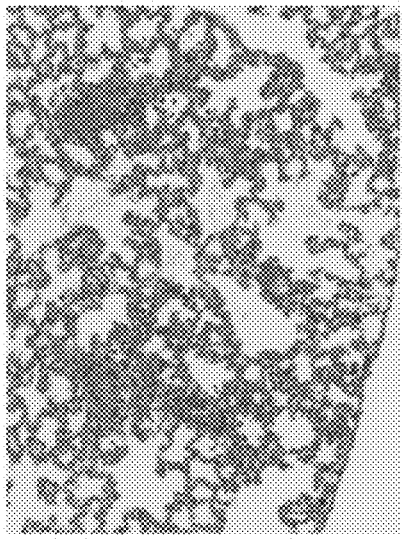
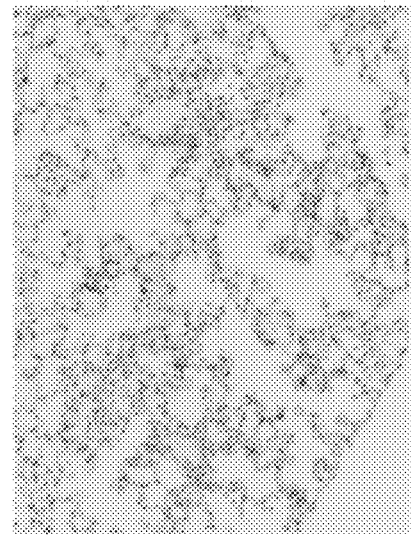
Fig 6

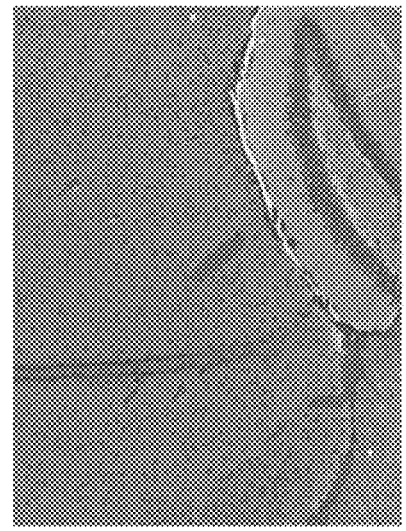
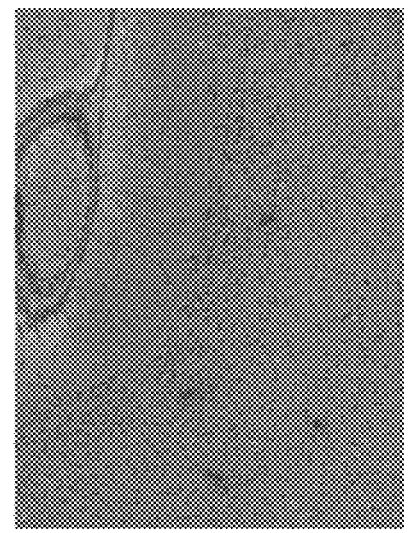
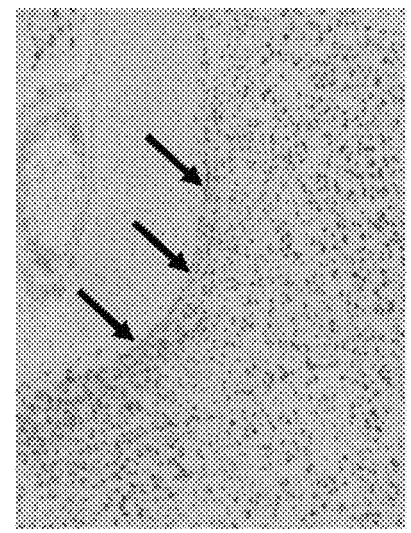
Fig 8

THERAPY FOR REDUCING BRAIN DAMAGE

FIELD

The present disclosure relates to a therapy for lung tissue damage based on local application of a leptin antagonist to the lungs.

BACKGROUND

COVID 19 is primarily a respiratory disease which is caused by a novel coronavirus, SARS-CoV-2, which binds to the ACE2 receptor on alveolar epithelial cells through its spike, S protein. The resulting pulmonary pathology is characterized by progressive deleterious remodeling in the lung tissue, local and systemic elevation of cytokine levels, acute lung inflammation, systemic vasculitis and coagulopathy. The acute phase of COVID 19 disease can be associated with neurological symptoms, which are related to SARS-CoV-2 invading brain neurons via the nasal turbinate epithelium and olfactory nerves. Furthermore, about one third of coronavirus infected patients exhibit post-disease late neurological symptoms.

Hypertension and obesity, both associated with inflammation, have been shown to correlate with the severity of COVID 19 disease. Notably, elevated circulating leptin level is a hallmark of obesity. Leptin and leptin receptor were shown to be overexpressed in viral infections such as HIV, and leptin was found to be a mediator of the pathogenesis of the severe 2009 pandemic influenza A (H1N1) infection, which was associated with cytokine dysregulation. Moreover, leptin promotes venous and arterial thrombosis that frequently occur in COVID 19 patients.

Deleterious tissue remodeling takes place in the wall of lung alveoli as part of the response to coronavirus infection. This process is characterized by local massive infiltration of inflammatory monocytes and macrophages, local ROS synthesis, cytokine accumulation and neutrophil activation. Also, leptin hormone and leptin receptor are synthesized locally at the site of injury.

A leptin antagonist that attaches to locally available leptin receptors generates an inactive complex. Thus, leptin antagonists have been shown effective in protecting cellular and tissue integrity when administered locally to the aortic wall prone to medial degeneration leading to aortic aneurysm.

However, the effect of a leptin antagonist on lung tissue infected by coronavirus and the efficacy of a leptin antagonist in treating subsequent lung tissue damage and related complications, such as direct neuro-invasion or via a remote inflammatory response as elicited by the primary lung event, are still enigmatic.

SUMMARY

Embodiments of the disclosure provide a method for treatment of damaged lung tissue by administering a leptin antagonist (LepA) locally to the upper airways and/or to the lung. Typically, the LepA is administered in an inhalable composition, namely, an aerosol, which may be a wet aerosol (e.g., LepA dissolved in physiological saline solution, e.g., 0.9% saline, as a solute) or a dry inhalable composition (powder).

In some embodiments, the LepA is administered via aerosol by using a nebulizer for spontaneous manual breathing, or by introducing the aerosol through ventilatory support, e.g., by using a mechanical respirator, in cases of severe respiratory failure or unconscious patients.

Embodiments of the disclosure provide treatment for acutely damaged lungs of a patient, e.g., a patient with a viral infection (e.g., coronavirus) and/or a bacterial infection and/or a parasitic pathogen or a patient whose lung tissue was damaged by exposure to a chemical, and a patient with acute respiratory distress syndrome (ARDS).

In some embodiments, the disclosure provides a method for treatment of a coronavirus infected patient by administering a leptin antagonist (LepA) locally to the patient's upper airways and lungs.

The LepA may be administered to the patient daily, e.g., once or twice a day. In some embodiments an effective delivered daily dose (administered to the lungs) of about 10-100 μg LepA is applied to the lungs in an inhalable composition (e.g., dissolved in 0.9% saline solution or as a dry powder).

The treatment, according to embodiments of the disclosure, may be useful, among others, for reducing viral load in the lung, for reducing inflammation in the lung, for preserving integrity and viability of alveolar cells of the lung, for protecting organs remote from the lung from a cytokine storm, and for reducing viral load in remote organs, such as the brain.

Embodiments of the disclosure provide an inhalable composition which includes LepA, for local application to lung tissue. The composition may include the LepA in a saline solution or as a dry powder. The composition, for human subjects, may include an effective delivered dose of about 10-100 μg LepA delivered to the lungs. In one embodiment, the composition includes an effective LepA dose in the range of 10-100 μg to be delivered to the lung alveolar cells and to nasal and olfactory epithelium and nerve cells.

The term "leptin antagonist" includes an agent capable of down-regulating leptin activity in a tissue, typically, through local administration to the tissue. For example, leptin antagonist may include at least one of the following agents capable of binding to and/or degrading leptin or leptin receptor; or an agent capable of down-regulating leptin and/or leptin receptor expression at the DNA or RNA level. In some embodiments the leptin antagonist is a 16KD recombinant protein, a mutant of the naturally synthesized leptin hormone, that has been designed for local application to be administered selectively, thus affecting the involved tissue only, without any traceable or functional impact on surrounding or remote tissues.

BRIEF DESCRIPTION OF THE FIGURES

The disclosure will now be described in relation to certain examples and embodiments with reference to the following illustrative figures so that it may be more fully understood. In the figures:

Figure 1:
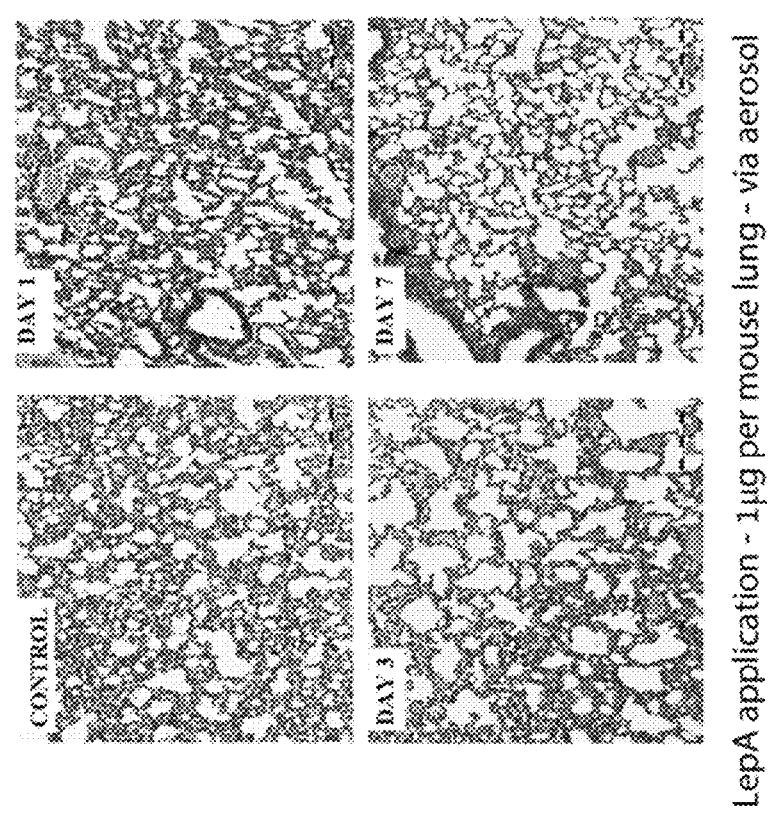

FIG. 1 shows, in Example 1, a time course analysis that demonstrates that LepA treatment preserved tissue integrity and cellular viability;

Figure 4:
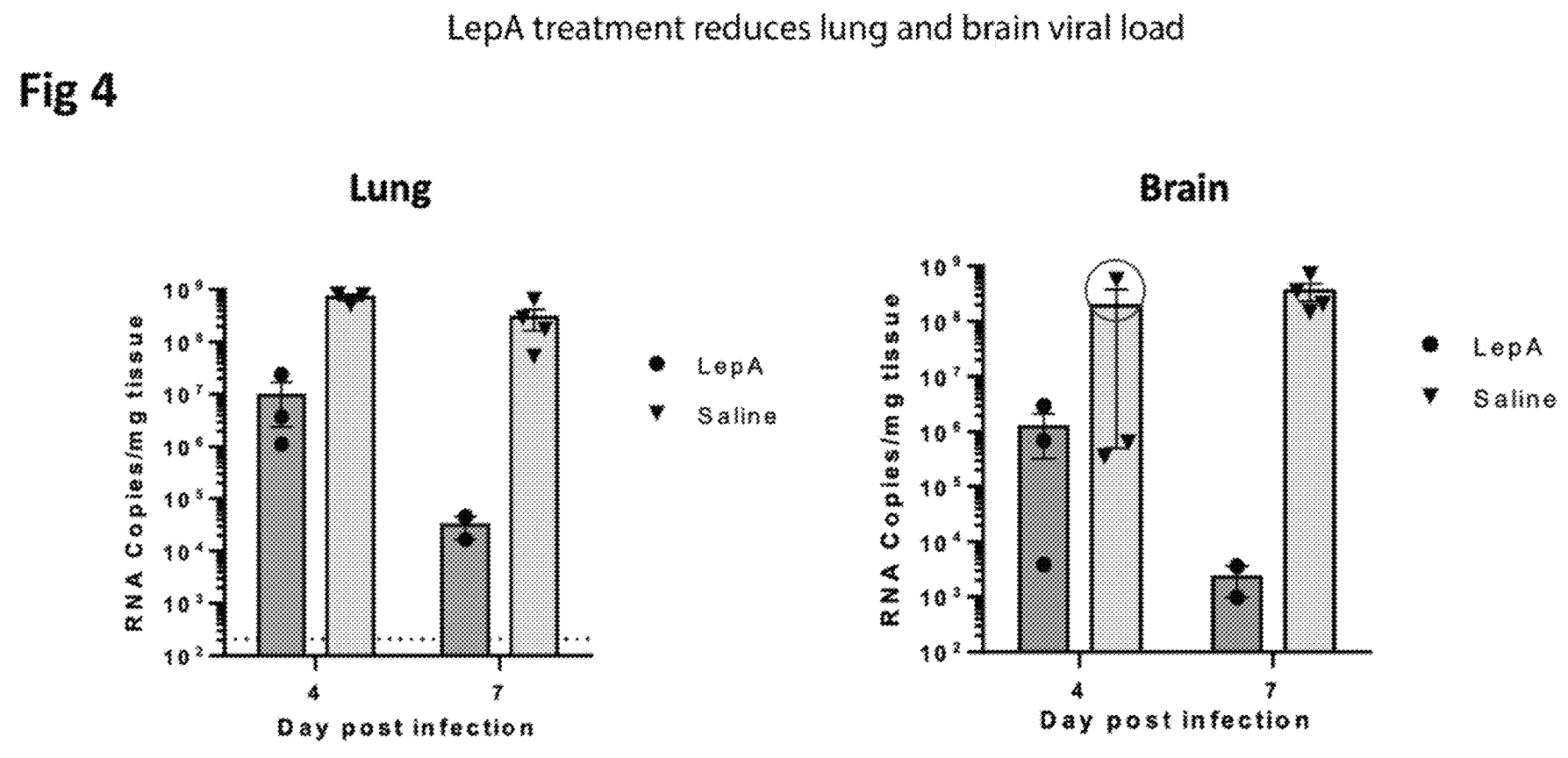

FIG. 4 shows, in Example 2, the viral load in lung and brain tissue of K18-hACE2 transgenic mice treated with saline or LepA, at day 4 and 7 post SARS-CoV-2 inoculation (10^6PFU), with LepA treatment initiated 12 h post inoculation;

FIG. 6 shows, in Example 2, IHC/SARS-CoV-2 Spike and H&E of lung tissue of a K18-hACE2 transgenic mouse at day 7 post SARS-CoV-2 inoculation (10^6PFU), with LepA treatment initiated 12 h post inoculation;

FIG. 8 shows, in Example 2, IHC/SARS-CoV-2 Spike and H&E of brain tissue of a K18-hACE2 transgenic mouse at day 7 post SARS-CoV-2 inoculation (10^6PFU), with LepA treatment initiated 12 h post inoculation.

DETAILED DESCRIPTION

Figure 2:
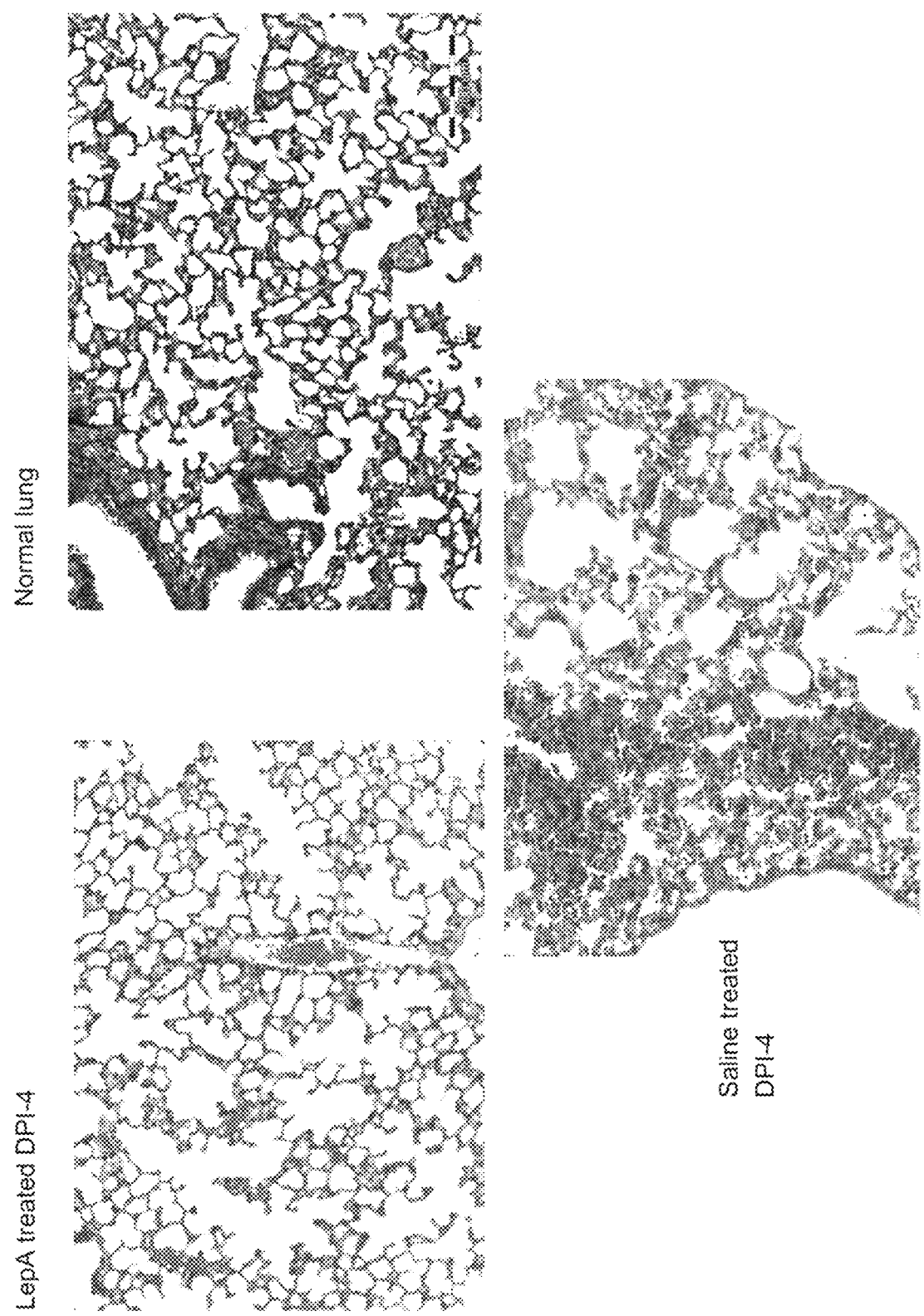
FIG. 2 shows, in Example 2, H&E of lung tissue of a K18-hACE2 transgenic mouse at day 4 post SARS COV-2 inoculation (10^6PFU), treated with LepA or saline solution.

Embodiments of the disclosure enable prevention and amelioration (collectively may be referred to as "treatment") of damage to lung and/or brain tissue.

Conditions such as, viral infection (and other infective agents), aseptic chemical damage, ARDS and others, may cause noxious stress, which elicits generation of ROS (reactive oxygen species) that damage live tissue cells. The JAK/STAT signaling pathway, which is driven by local activation of leptin/leptin receptor complex, is a key pathway affecting cells under these circumstances, promoting local inflammation and cellular apoptosis. Local LepA therapy protects and preserves the integrity and viability of live cells that have been damaged by noxious stress.

One embodiment of the disclosure enables treatment of damage to tissue due to tissue remodeling, e.g., following an infection of lung tissue, such as the coronavirus infection.

In one embodiment, a method for treatment of a coronavirus infected patient, is provided. The method includes locally administering of leptin antagonist to the patient's airways (e.g., upper airways and lungs).

One embodiment of the disclosure provides a composition containing a leptin antagonist (LepA) for local application to damaged tissue. In one embodiment the composition includes LepA dissolved in 0.9% saline solution. In another embodiment the composition includes dry microscopic powder of LepA. Typically, the composition is designed to be administered in aerosol form.

The method for treatment of a coronavirus infected patient and the composition described above may also be useful for one or more of the following: reducing viral load in the patient's lung, reducing inflammation in the patient's lung, preserving integrity and viability of distal bronchial and alveolar epithelial cells of the patient's lungs, blocking cytokine synthesis in the damaged lung cells, preventing systemic increase of cytokine levels thereby preventing a cytokine storm that is known to affect organs remote from the patient's lung, reducing viral load in the patient's brain and reducing coronavirus neuro-invasion through the patient's nasal and olfactory epithelium and nerve cells, and also reducing blood hypercoagulability, which is known to promote venous and/or arterial thrombosis.

Leptin antagonist refers to an agent capable of down-regulating leptin activity in a tissue, typically, through local administration to the tissue. Such an agent may include a molecule, compound or element capable of locally binding to and/or degrading leptin or leptin receptor, as well as a molecule, compound or element capable of locally down-regulating leptin and/or leptin receptor expression at the DNA or RNA level (i.e., agents capable of locally blocking transcription or translation). In the embodiments exemplified herein, LepA includes muteins (mutants) of a native mammalian leptin, e.g., a recombinant 16KD protein, a mutant of the naturally synthesized leptin hormone that is able to bind to the leptin receptor, with similar or higher affinity like SMLA (superactive mouse leptin antagonist) and SHLA (superactive human leptin antagonist) presenting 60 fold higher affinity to the leptin receptor compared to the native endogenous leptin, but the complex formed lacks the efficacy to activate it. Thus, this mutant blocks or dampens the activity of endogenous leptin. In one embodiment a mutant of the human leptin hormone is used, such as the super-active human leptin antagonist SHLA (distributed by PLR Ldt., e.g., Cat. no. SLAN-2 GENE ID 3952 or Cat. no. SLAN-1 GENE ID 16846).

The therapeutically effective amount (effective delivered amount) of LepA in the composition may vary depending on the organ and specifically on the size of the tissue destined for therapy. Local direct application of LepA to the target tissue requires lower doses compared to selective LepA administration intra-arterially to address a well-defined damaged tissue in an isolated organ. In embodiments of the disclosure, LepA therapy is used for local application only (e.g., via aerosol) and not by systemic dissemination. In one embodiment, e.g., when used for treatment of a patient infected by coronavirus (e.g., COVID 19), an effective delivered dose of LepA 10-100 μg is delivered to the lungs (possibly, per daily treatment) via direct inhalation.

In one embodiment the composition includes SHLA (superactive human leptin antagonist).

As used herein, the term "administration" means introduction of a prescribed amount of LepA to a patient's lungs, e.g., via an aerosol device, inhaler device, ventilator or another device capable of delivering the active ingredients (e.g., LepA and possibly other therapeutic agents) to a patient's upper airways and lungs.

Compositions according to embodiments of the disclosure may be specifically designed to target the lung. For example, the composition may be in aerosol form. The use of inhaled aerosols allows selective treatment of the lungs directly by achieving high drug concentrations in the lower airways.

Aerosols having a mass median aerodynamic diameter (MMAD) of less than 4.5 μm are used for effective targeting of the small bronchi and bronchioles. Aerosols having a smaller size MMAD should be advantageous for deposition of microdroplets distally, in the lung alveoli. According to one embodiment of the disclosure, an inhalable composition for effective local application to upper airways and lung tissue, includes a leptin antagonist and has aerosol droplets with an MMAD of 1.5 μm. In some embodiments, the composition has aerosol droplets with an MMAD in the range of 1.5-4.5 μm.

In some embodiments, non-carrier based dry powder compositions may be used. The composition may include lyophilized LepA as a dry powder and the method for treatment of a patient infected by coronavirus or treatment of a damaged (e.g., from any reasons) lung, includes the use of a dry powder inhaler to deliver the composition to a patient's lung tissue. In some embodiments, a carrier-based composition of LepA for administration with a dry powder inhaler is provided.

In some embodiments, a carrier-based composition containing LepA and a force control agent for administration with a dry powder inhaler is provided. In some embodiments, a carrier-based composition of LepA for administration with a dry powder inhaler is provided, wherein the fine particle fraction (FPF) is less than 1.5 µm and in some embodiments, less than 0.5 µm.

In some embodiments, the inhalable composition has a FPF where more than 50% of the particles are smaller than 1.5 µm.

Compositions according to embodiments of the disclosure may be packaged in various suitable containers for administration to the patient. For example, the composition may be filled into a capsule containing a total dose for administration. The capsule may be designed for pulmonary administration by the patient by using a dry powder inhaler device or other suitable pulmonary administration device.

In some embodiments, pressurized metered dose inhalers, soft mist inhalers and smart mist inhalers may be used for administration of LepA. For mist inhalers, aqueous-based solutions may be used. In one embodiment, LepA dissolved in 0.9% saline solution is administered to a patient, e.g., via a nebulizer, an inhaler or a ventilatory support. A nebulizer may be used for spontaneous manual breathing, while a ventilatory support, e.g., a mechanical respirator, may be used in patients with severe respiratory failure or unconscious patients.

The inventors of the present disclosure have shown that administering a leptin antagonist (LepA) locally via aerosol to the lungs in coronavirus infected mice, reduced the viral load, facilitated viral clearance and diminished expression of pro-inflammatory cytokines in the lungs. Inhibition of cytokine synthesis by the affected lung cells, is expected to reduce systemic cytokine levels in coronavirus infected subjects, thus preventing systemic cytokine storm, vasculitis, systemic coagulopathy, and damage in remote organs, such as the heart, kidney brain and muscle.

LepA treatment via aerosol was found effective in protecting the brain from viral infection, severe inflammation and cellular damage reduction. This was notably achieved by preventing direct penetration of the virus into the CNS via the olfactory bulb. LepA treatment was also found effective in reducing viral load in a patient's brain and reducing coronavirus neuro-invasion through the patient's nasal and olfactory epithelium and nerve cells.

In the examples described below, beneficial effects of LepA in protecting or treating damaged lung and/or brain tissue during SARS-CoV-2 infection, were shown, using a human ACE2 transgenic mouse model.

The LepA used in the experiments described herein includes SMLA, namely, the mouse version, which is structurally and functionally similar to the human version, SHLA.

The leptin antagonists SHLA and SMLA have a 60-fold higher affinity to the leptin receptor compared with endogenous leptin. In previous experiments using SMLA, there were no signs of toxicity, no evidence of systemic leakage to the peripheral circulation, nor systemic hormonal perturbations.

The following examples illustrate advantageous properties of LepA in treating damaged tissues, protecting tissues from infection (e.g., viral and/or bacterial infection of the lungs), facilitating effective clearance of a viral infection in an infected tissue as well as aspects of how the disclosure may be carried-out in practice. These examples are not intended to limit the scope of the disclosure.

EXAMPLE 1

Example 1 demonstrates safety of LepA aerosol therapy as applied to the lungs in mice that were monitored thereafter for 7 days.

Materials and Methods:

Wild type C57BL/6 mice were used in this experiment. The mice were exposed to LepA that was administered to the lungs via aerosol (delivering approx. 1 µg LepA per mouse/lung). 1 mg LepA was dissolved in 0.9% saline solution and introduced into a clinically high-grade eFlow rapid Nebulizer System (PARI). After treatment, the mice were followed up and selected mice were sacrificed on day 1, 3 and 7 post therapy, to assess lung histology.

Results:

Histological results shown in FIG. 1 display a time course analysis that demonstrates preserved tissue integrity and cellular viability. There were also no signs suggestive of compromised lung function. All mice presented normal behavior following LepA aerosol therapy.

EXAMPLE 2

Example 2 demonstrates the results of LepA aerosol therapy administered to the lungs of human ACE2 transgenic mice, after they were inoculated with a high dose of SARS-CoV-2 virus ($10^6$ PFU) (WA1/2020 strain). LepA was administered via aerosol once daily (estimated dose delivered to the lungs per mouse/day was 1 µg) for 7 consecutive days. The results provide evidence of decreased viral load, decreased inflammation changes, and inhibited cytokine (TNFα and IL-6) synthesis in the lungs. Results of the experiments in Example 2 also showed that LepA aerosol treatment decreases viral load in the brain and prevents direct neuro-invasion of the virus into the CNS (central nervous system). This, most likely, has been achieved also by the impact of inhaled LepA via the upper airways, protecting the epithelial cells lining of the nasal turbinate, and directly via the olfactory nerves.

Materials and Methods:

Studies have shown that SARS-CoV-2 enters human cells by binding to human angiotensin-converting enzyme 2 (ACE2). Transgenic hACE2 mice have been generated by introducing the human ACE2-coding sequence under the control of the human cytokeratin 18 (K18) promoter into wild-type mice to produce an hACE2 transgenic mouse strain. ACE2 expression was observed in the infected airway epithelial cells. It has been shown by the inventors of the present disclosure and others, that intranasal inoculation of K18-hACE2 transgenic mice with SARS-CoV-2 facilitates neuro-invasion. Cause of death upon infection in this model is unclear, and unlikely to be driven by lung-induced pathology or pneumonia. In this model however, the lungs and brain are severely infected by SARS-CoV-2. The infection begins in the airway epithelium, spreads to the lower respiratory tract and later on spread to the brain. The infection causes infiltration of macrophages and lymphocytes in the lungs and up-regulation of pro-inflammatory cytokines and chemokines in the lungs and brain. Following infection, K18-hACE2 mice were shown to lose weight rapidly, become lethargic and dyspneic.

To investigate the efficacy of LepA treatment administered to the lungs in COVID 19, a mouse model of SARS- CoV-2 infection (K18-hACE2) was used. ACE2 TG mice were purchased from Jackson laboratories. Twenty mice were inoculated intranasally by SARS-CoV-2 virus ($10^6$ PFU).

Phase I:

The superactive mouse leptin antagonist (SMLA)-LepA (n=10) or saline (n=10) were administered via aerosol for 3 consecutive days.

LepA therapy was initiated 24 hours after intra-nasal inoculation of the virus.

Five mice from each group were sacrificed on day-post-inoculation (DPI)-4, and the survivors euthanized on DPI-11.

Phase II:

LepA therapy was administered 12 hours after inoculation with the virus (instead of 24 hours interval used in phase I). Also, the duration of LepA therapy was extended from 3 to 7 days.

Phase I Results:

Histological examination, including immunohistochemistry (IHC) and histochemistry using hematoxylin and eosin (H&E) staining of lung and brain tissue were performed on DPI-4 and DPI-11 mice.

FIG. 2 shows H&E of LepA treated lung tissue DPI-4 (top left) vs. saline control lung tissue DPI-4 (bottom) vs. normal lung tissue (top right), demonstrating that the LepA treated tissue appears undamaged (the same as the normal lung tissue) whereas the saline treated tissue is damaged.

Viral load, IL-6 and TNFα mRNA levels were assessed in DPI-4 mice.

Figure 3B:
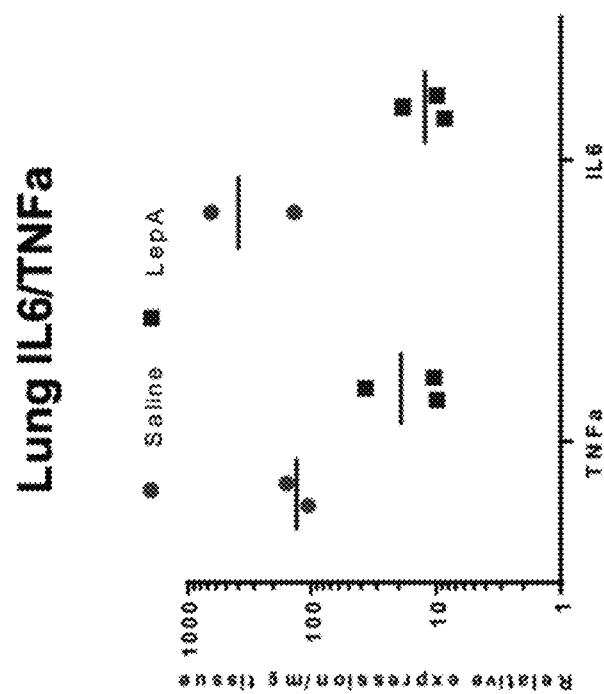
FIG. 3B summarizes, in Example 2, the expression of TNFα and IL6 mRNA in saline-treated vs. LepA-treated lung tissue of K18-hACE2 mice at day 4 post SARS-CoV-2 inoculation, with LepA treatment initiated 24 h post inoculation.
Figure 3A:
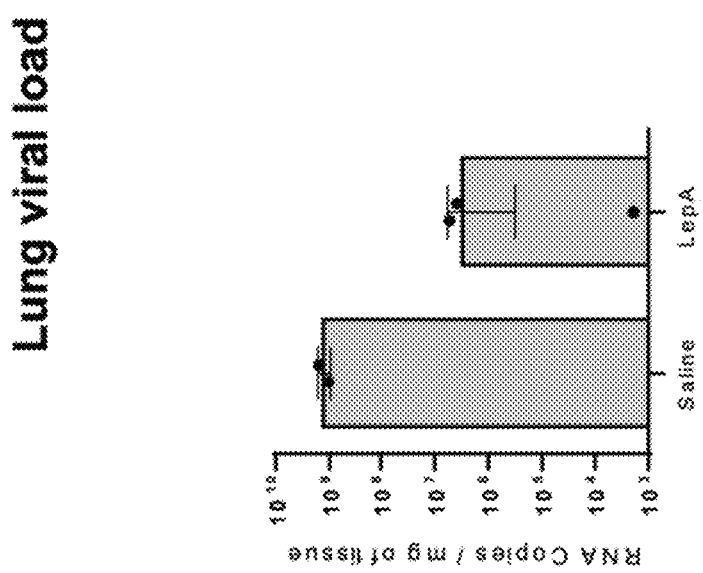
FIG. 3A shows, in Example 2, the viral load in lung tissue of K18-hACE2 transgenic mice treated with saline or LepA, at day 4 post SARS-CoV-2 inoculation (10^6PFU), with LepA treatment initiated 24 h post inoculation.

FIG. 3A shows the viral load in lung tissue treated with saline vs. tissue treated with LepA. It was demonstrated that in LepA-treated mice lung tissue shows viral load reduced to below $10^7$ viral RNA copies/mg tissue, whereas saline-treated lung tissue shows a much higher viral load. Tissue having a viral load of less than $10^7$ viral RNA copies/mg tissue are not productively infected (as demonstrated by histology), thus, it has been concluded that LepA treated lungs exhibited lower viral load and absence of active viral replication compared to the saline-treated controls.

FIG. 3B summarizes the mRNA expression of TNFα and IL6 in saline-treated vs. LepA-treated lung tissue, in DPI-4 mice. Both TNFα and IL6 expression were lower in lungs from LepA-treated vs. saline-treated mice, showing a correlation between viral load and TNFα/IL6 expression. These results show a clear effect of the LepA treatment of SARS-CoV-2 infected mice and suggest that LepA treatment protects lung tissue from excessive inflammation.

Phase II Results:

FIG. 4 shows the viral load in lung and brain tissue of K18-hACE2 transgenic mice treated with saline or LepA, on day 4 and 7 post SARS-CoV-2 inoculation ($10^6$PFU). LepA treatment was initiated 12 h post inoculation. The results shown in FIGS. 3A and 4 demonstrate that LepA treatment reduces lung and brain viral load.

Figure 5:
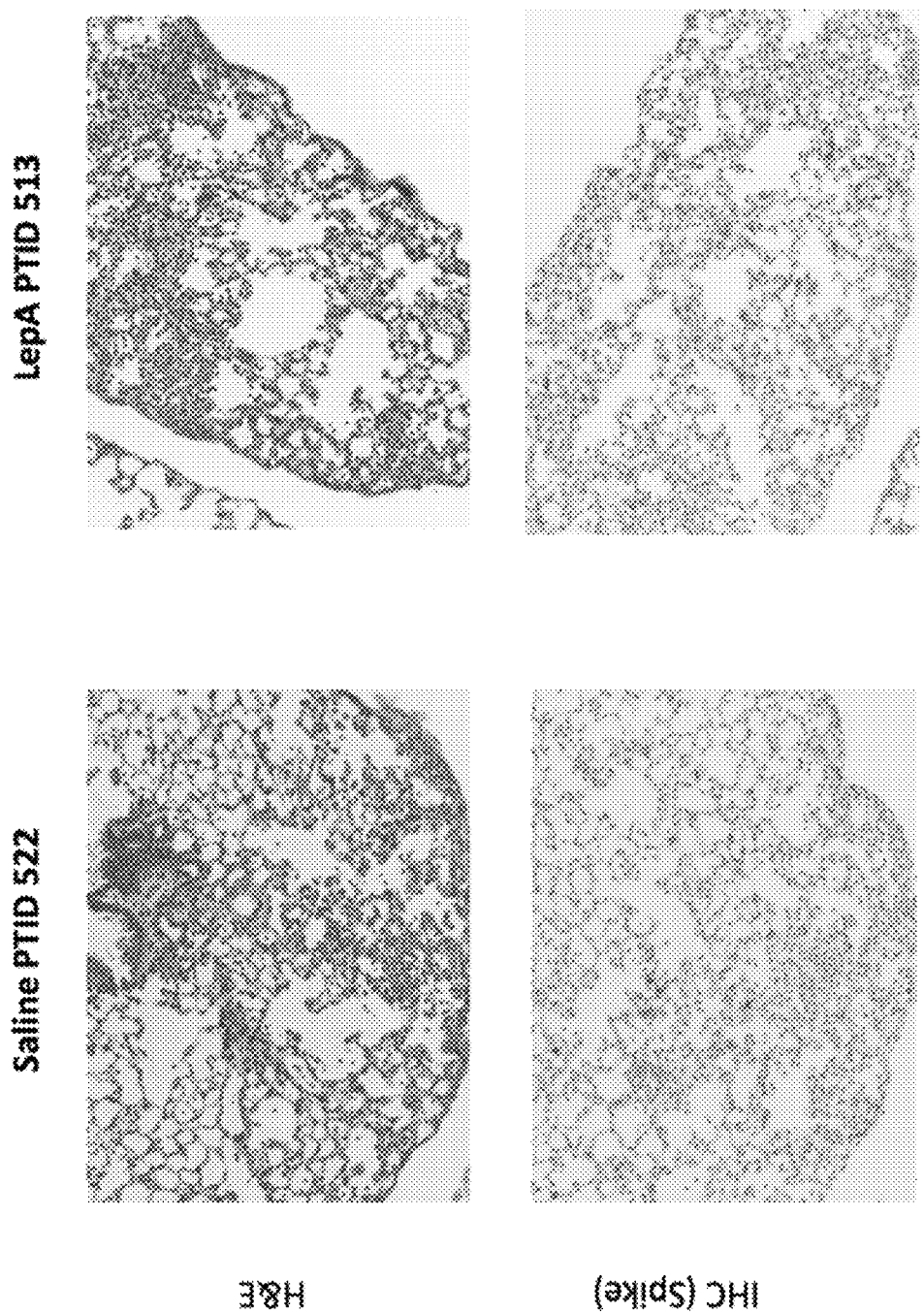
FIG. 5 shows, in Example 2, IHC/SARS-CoV-2 Spike and H&E of lung tissue from mice at day 4 post SARS-CoV-2 inoculation (10^6PFU) with LepA treatment initiated 12 h post inoculation.

FIG. 5 shows IHC/SARS-CoV-2 Spike (bottom) and H&E (top) of lung tissue from saline treated (control) mice vs. LepA treated mice at DPI-4.

FIG. 6 shows IHC/SARS-CoV-2 Spike (bottom) and H&E of lung (top) tissue from LepA treated mice at DPI-7.

Figure 7:
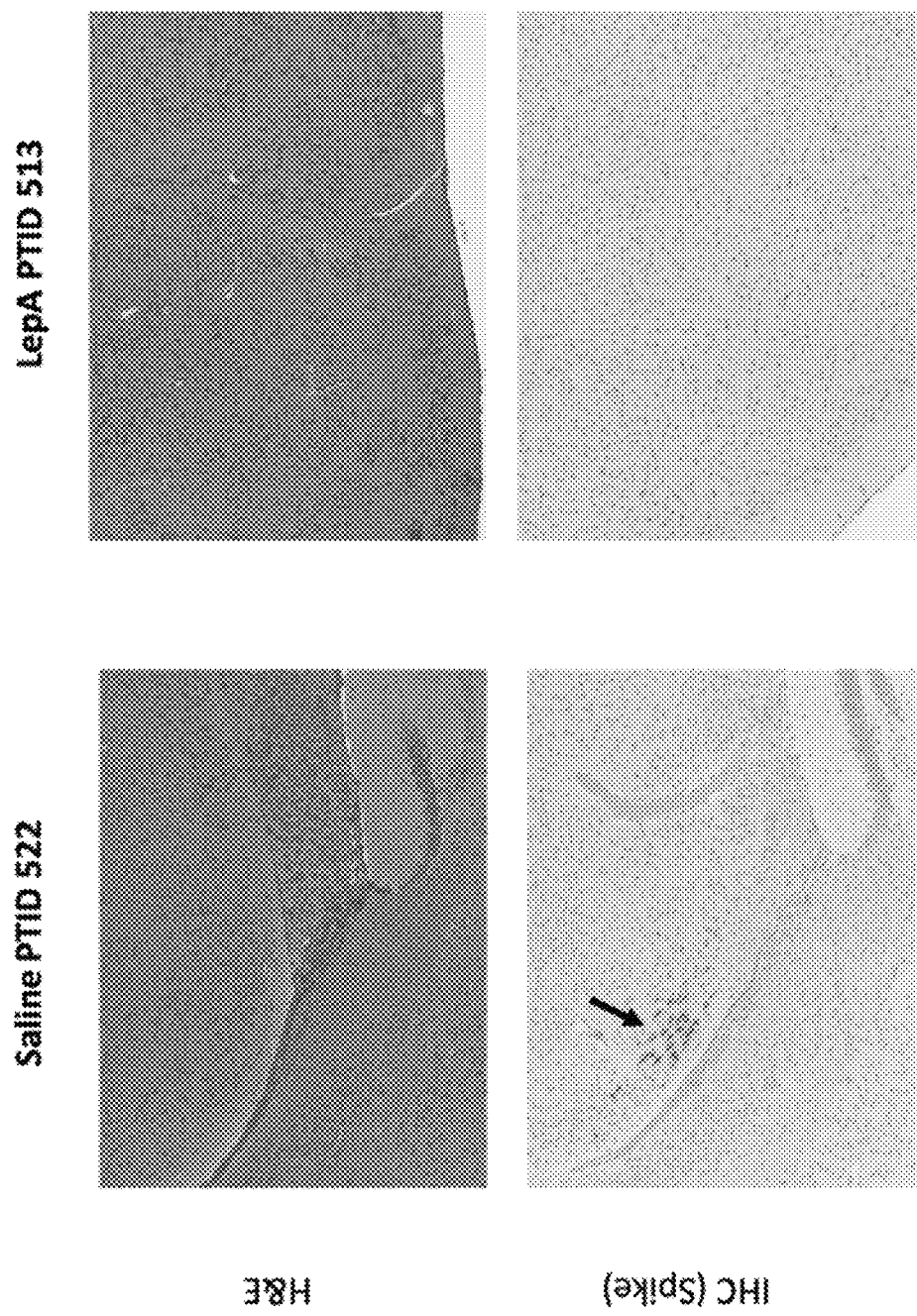
FIG. 7 shows IHC/SARS-CoV-2 Spike and H&E of brain tissue of a K18-hACE2 transgenic mouse at day 4 post SARS-CoV-2 inoculation (10^6PFU), with LepA treatment initiated 12 h post inoculation.

FIG. 7 shows IHC/SARS-CoV-2 Spike (bottom) and H&E (top) of brain tissue from saline treated mice vs. LepA treated mice at DPI-4.

FIG. 8 shows IHC/SARS-CoV-2 Spike (bottom) and H&E of brain (top) tissue from LepA treated mice at DPI-7.

LepA-treated mice demonstrated no viral Spike antigen in the brain on DPI-4 and DPI-7 whereas saline-treated mice exhibited the coronavirus Spike antigen on DPI 4 (marked by the arrow in FIG. 7) and at much higher density on DPI-7 (marked by the arrows in FIG. 8).

Analysis of the olfactory bulb revealed that LepA-treated mice rarely exhibit the presence of viral Spike antigen on DPI-4 and none on DPI-7, while saline-treated mice presented abundance of viral antigen in the olfactory bulb at both timepoints.

These results show that LepA facilitates viral clearance from the lungs and protects the brain from neuro-invasion.

No difference in weight loss or survival was demonstrated between the LepA treated and control mice. Notably, mortality was not an endpoint in this study, as some evidence suggest that ACE2 TG mice most likely die from causes other than pulmonary insufficiency or neurological damage.

The examples described herein demonstrate that LepA treatment of coronavirus infected animals protects against severe lung inflammation, reduces viral load and facilitate viral clearance, and prevents IL-6 and TNFα mRNA upregulation in lung tissue.

On the basis of the above results, it can be deduced that selective local LepA therapy via aerosol inhalation provides advanced protective benefits during SARS-CoV-2 infection and likely, as well, in a variety of lung infections, by other viruses and pathogens. Also, this therapy should provide beneficial effects protecting cellular integrity, viability and function in cases of chemical lung damage and ARDS (acute respiratory distress syndrome), by any cause.

LepA aerosol therapy, provided by embodiments of the disclosure is short acting and applied locally to the affected tissue, to rescue the damaged lung tissue without systemic LepA dissemination. Although applied locally, counteracting deleterious remodeling and local inflammation in the damaged lung tissue, the treatment consequently attenuates systemic cytokine storm, preventing vasculitis, systemic coagulopathy, and damage to remote organs and tissues. Thus, embodiments of the disclosure provide an effective and safe therapy to damaged lung and/or brain tissue and may be used to effectively and safely treat coronavirus infected patients.

The invention claimed is:

1. A method for treating or reducing damage to brain tissue of a SARS-CoV-2 infected patient, the method comprising administering a leptin antagonist (LepA) locally to the patient's nasal and olfactory epithelium and nerve cells, wherein said LepA is a superactive leptin antagonist selected from a superactive human leptin antagonist (SHLA) and a superactive mouse leptin antagonist (SMLA), and wherein said SHLA comprises SLAN-2 GENE ID 3952 and said SMLA comprises SLAN-1 GENE ID 16846.

2. The method of claim 1, comprising administering the LepA in an inhalable composition via aerosol.

3. The method of claim 2, wherein administering LepA via aerosol comprises using a nebulizer, an inhaler or a ventilatory support.

4. The method of claim 2, comprising administering to the patient an effective delivered LepA dose, within a range of about 10-100 µg.

5. The method of claim 2, wherein the inhalable composition has a mass median aerodynamic diameter (MMAD) within a range of 1.5-4.5 µm.

6. The method of claim 2, wherein the inhalable composition has a FPF (fine particle fraction) where more than 50% of the particles are smaller than 1.5 µm.

7. The method of claim 2, wherein the inhalable composition comprises a dry powder.

8. The method of claim 2, wherein the inhalable composition comprises physiological saline solution as a solute.

9. A method for treating or reducing damage to brain tissue of a SARS-CoV-2 infected patient, the method comprising locally administering a LepA to the patient's nasal cavity, said LepA being a mutant of a naturally leptin hormone capable of binding a leptin receptor and to form an inactivated complex therewith: wherein said LepA is a superactive leptin antagonist selected from a superactive human leptin antagonist (SHLA) and a superactive leptin leptin antagonist (SMLA), and wherein said SHLA comprises SLAN-2 GENE IS 3952 and said SMLA comprises SLAN-1 GENE ID 16846.

10. The method of claim 1, useful for reducing or treating neuro invasion of the SARS-CoV-2 virus by reducing viral load in the patient's brain.

* * * * *